(12) United States Patent
Markussen

(10) Patent No.: US 9,724,478 B2
(45) Date of Patent: Aug. 8, 2017

(54) INJECTION DEVICE FOR DELIVERING A FIXED DOSE OF LIQUID DRUG

(71) Applicant: Novo Nordisk A/S, Bagsvaerd (DK)

(72) Inventor: Tom H. Markussen, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 132 days.

(21) Appl. No.: 14/293,284

(22) Filed: Jun. 2, 2014

(65) Prior Publication Data

US 2014/0276598 A1 Sep. 18, 2014

Related U.S. Application Data

(63) Continuation of application No. 12/808,536, filed as application No. PCT/EP2008/068078 on Dec. 19, 2008, now Pat. No. 8,771,237.

(60) Provisional application No. 61/019,660, filed on Jan. 8, 2008.

(30) Foreign Application Priority Data

Dec. 20, 2007 (EP) ..................... 07150207

(51) Int. Cl.
*A61M 5/315* (2006.01)
*A61M 5/24* (2006.01)

(52) U.S. Cl.
CPC ........ *A61M 5/3157* (2013.01); *A61M 5/3155* (2013.01); *A61M 5/3156* (2013.01); *A61M 5/31591* (2013.01); *A61M 5/24* (2013.01); *A61M 5/31501* (2013.01); *A61M 5/31551* (2013.01); *A61M 5/31585* (2013.01); *A61M 2005/2407* (2013.01); *A61M 2005/2492* (2013.01); *A61M 2205/581* (2013.01); *A61M 2205/582* (2013.01)

(58) Field of Classification Search
CPC ............. A61M 5/3155; A61M 5/3156; A61M 5/31591; A61M 5/31501; A61M 5/31551; A61M 5/24; A61M 5/3157; A61M 5/31538
USPC ...................................... 604/506
See application file for complete search history.

(56) References Cited

U.S. PATENT DOCUMENTS

| | | | |
|---|---|---|---|
| 5,244,465 A | * | 9/1993 | Michel .................. A61M 5/24 604/187 |
| 5,725,508 A | | 3/1998 | Chanoch et al. |
| 6,235,004 B1 | | 5/2001 | Steenfeldt-Jensen et al. |
| 7,169,132 B2 | | 1/2007 | Bendek et al. |
| 7,195,616 B2 | | 3/2007 | Diller et al. |
| 2002/0016571 A1 | | 2/2002 | Kirchhofer et al. |
| 2007/0016142 A1 | | 1/2007 | Burren et al. |
| 2007/0088288 A1 | | 4/2007 | Barron et al. |

FOREIGN PATENT DOCUMENTS

| | | |
|---|---|---|
| EP | 702970 | 3/1996 |
| EP | 1645301 | 4/2006 |
| JP | 60-175249 U | 11/1985 |
| WO | 2004078241 | 9/2004 |
| WO | 2004/089450 A1 | 10/2004 |
| WO | 2006/024461 A1 | 3/2006 |
| WO | 2006/058883 A2 | 6/2006 |

(Continued)

*Primary Examiner* — Edelmira Bosques
(74) *Attorney, Agent, or Firm* — Leon Y. Lum

(57) ABSTRACT

An injection device for delivering a predetermined fixed dose of liquid drug, comprising a base member, a piston rod a first tubular member, and a second tubular member.

10 Claims, 10 Drawing Sheets

(56) References Cited

FOREIGN PATENT DOCUMENTS

WO      2006/072188 A1    7/2006
WO      2006/084876 A1    8/2006

\* cited by examiner

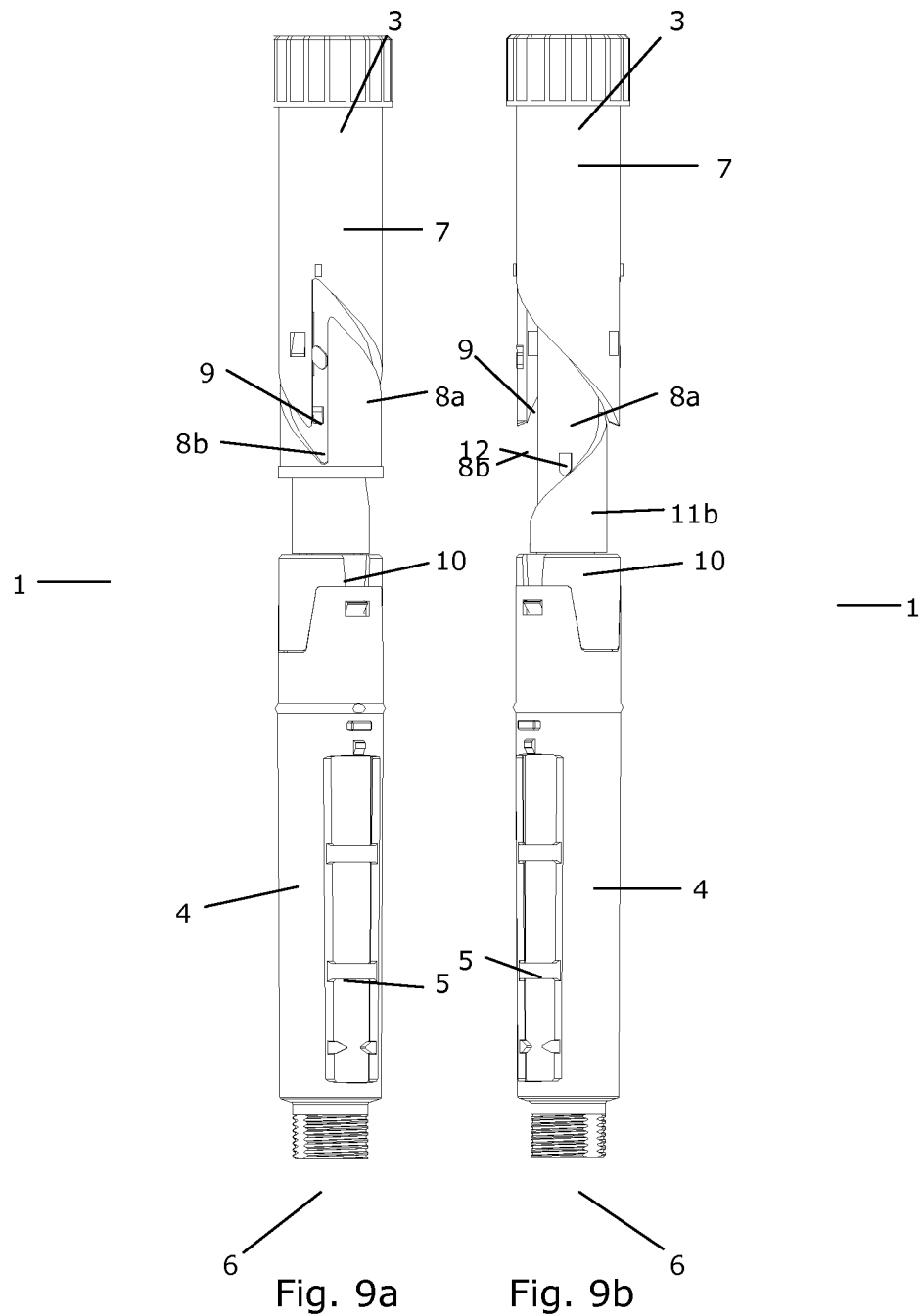

INJECTION DEVICE FOR DELIVERING A FIXED DOSE OF LIQUID DRUG

CROSS-REFERENCE TO RELATED APPLICATIONS

This application is a continuation of U.S. application Ser. No. 12/808,536, filed Oct. 21, 2010 which is a 35 U.S.C. §371 national stage application of International Patent Application PCT/EP2008/068078 (published as WO 2009/080775), filed Dec. 19, 2008, which claimed priority of European Patent Application 07150207.4, filed Dec. 20, 2007; this application further claims priority under 35 U.S.C. §119 of U.S. Provisional Application 61/019,660, filed Jan. 8, 2008, the contents of which are incorporated herein by reference.

FIELD OF THE INVENTION

The present invention relates to an injection device being adapted to deliver a fixed dose of a liquid drug. The injection device of the invention is particularly suitable for self-injection by the user of a liquid drug. Suitable drugs could be of a kind where significant variations in the required dose between individual injections are not expected. This may, e.g., be the case for drugs which need to be injected once a day or once a week. Medicaments suitable for this type of treatment include those having a biological profile which prohibits overdosing mainly because no, or only harmless side effects occur as a result of overdosing—A medicament comprising a GLP-1 compound is an example of such a medicament.

BACKGROUND OF THE INVENTION

U.S. Pat. No. 5,725,508 discloses a medication delivery pen having a reusable pen body assembly and a disposable cartridge assembly that are threadedly engageable with one another. A portion of the pen body assembly projects into the cartridge holder assembly for driving a cartridge plunger distances that are selected in accordance with a desired dose of medication to be delivered. The pen body assembly includes a generally cylindrical driver being slideably inserted in the housing, and a dose knob which is a hollow generally cylindrical structure. The dose knob is spline mounted over the driver within the housing of the pen body assembly, and relative rotation between the driver and the dose knob is thereby prevented.

A desired dose is set by rotating the dose knob, and during injection the dose knob also rotates. In order to prevent the piston rod from rotating during dose setting, but allowing it to rotate during injection, the pen body assembly comprises a clutch arrangement. The clutch arrangement constitutes additional mechanical parts of the medication delivery pen, and it renders the pen relatively complex to manufacture and operate.

Other similar injection devices are disclosed in WO 2006/058883 and WO 2006/084876, both disclosing injection devices in which a clutch arrangement being switchable between a dose setting mode and an injection mode is necessary in order to operate the injection properly.

US 2007/0088288 discloses a fixed dose injection pen. To execute a dose setting and ejection cycle using this pen a user has to perform four operations on the pen. First the dosage button must be rotated to a zero dose radial position relative to the housing. Thereafter the dosage button is pulled proximally out of the housing. Then the dosage button is rotated to a stop in order to set the dose, and finally the dosage button is pushed distally to eject the dose. This four-step dose setting and ejection procedure may be cumbersome to some users.

SUMMARY OF THE INVENTION

It is, thus, an object of the invention to provide an injection device which is mechanically simpler than similar prior art injection devices.

It is a further object of the invention to provide a mechanically simple injection device which is suitable for delivering a fixed dose of liquid drug.

It is an even further object of the invention to provide an injection device which is simpler to use and which requires less operations in order to execute a dose setting and ejection cycle than prior art fixed dose devices.

It is an even further object of the invention to provide an injection device comprising fewer components than similar prior art injection devices.

It is an even further object of the invention to provide an injection device which can be operated in a very reliable manner.

According to the invention the above and other objects are fulfilled by providing an injection device for delivering a predetermined fixed dose of liquid drug, the injection device comprising:
  a base member,
  a piston rod defining a longitudinal axis and being adapted to cooperate with a piston in causing the predetermined fixed dose to be delivered from the device,
  a first tubular member operatively coupled with the base member and movable to set the predetermined fixed dose,
  a second tubular member operatively coupled with the first tubular member and the piston rod,
wherein the base member, the first tubular member and the second tubular member are so coupled that a complete dose setting and ejection cycle is performed in two-steps consisting of rotating the first tubular member from a zero dose position to a predefined dose setting stop and advancing the first tubular member non-rotationally along the longitudinal axis to an ejection stop, and
wherein once the predetermined fixed dose has been set and the ejection has commenced, it is not possible to start setting a new dose until the entire predetermined fixed dose has been ejected.

By such an arrangement the user does not have to worry about finding the zero point from which the dose setting can begin every time a new dose setting and ejection cycle is to be carried out. Furthermore, the arrangement provides for a very simple operation of the device as the dose setting member is first rotated to a dose setting stop to set the predetermined fixed dose, and thereafter advanced axially to an ejection stop to eject the set dose. Hence, the user does not have to worry about visually controlling the dose setting, e.g. by reading a scale or the like. Even further, due to the fact that the first tubular member does not rotate during its advancement along the longitudinal axis when the device is manipulated to deliver the predetermined fixed dose the user does not feel a rotation when pressing directly on the first tubular member. It is thus possible to avoid incorporating a rotationally decoupled push button at the proximal end of the first tubular member. Even further, it is guaranteed that the predetermined fixed dose, and only the predetermined fixed dose, is delivered each time the device undergoes one dose setting and ejection cycle.

In one aspect of the invention an injection device for delivering a predetermined fixed dose of liquid drug is provided, the injection device comprising:
- a base member,
- a piston rod defining a longitudinal axis and being adapted to cooperate with a piston in causing the predetermined fixed dose to be delivered from the device,
- a first tubular member operatively coupled with the base member and movable to set the predetermined fixed dose,
- a second tubular member operatively coupled with the first tubular member and the piston rod, wherein during dose setting the first tubular member is allowed to rotate with respect to the base member from a zero dose position to a predefined dose setting stop and during injection the first tubular member is allowed to advance non-rotationally along the longitudinal axis while the second tubular member is allowed to rotate with respect to the base member.

In an embodiment of the invention an injection device for delivering a predetermined fixed dose of liquid drug is provided, the injection device comprising:
- a base member,
- a piston rod adapted to cooperate with a piston in causing the predetermined fixed dose to be delivered from the device,
- a first tubular member engaging the base member via a first track and a first protruding part, one of the first track and the first protruding part being arranged on an outer surface of the first tubular member, and the other of the first track and the first protruding part being arranged on the base member, said first protruding part engaging the first track, the first tubular member being movable to set the predetermined fixed dose,
- a second tubular member engaging the first tubular member via a second track and a second protruding part, one of the second track and the second protruding part being arranged on an outer surface of the second tubular member, and the other of the second track and the second protruding part being arranged on an inner surface of the first tubular member, said second protruding part engaging the second track, the second tubular member further being rotationally locked to the piston rod, wherein the first track comprises a first portion which the first protruding part travels during setting of the predetermined fixed dose, and the second track comprises a first portion which the second protruding part travels during setting of the predetermined fixed dose, and wherein the first portion of the first track and the first portion of the second track are shaped in such a manner that, during setting of the predetermined fixed dose, angular and axial movements of the first tubular member relatively to the base member correspond to angular and axial movements of the first tubular member relatively to the second tubular member.

Employing such tracks and protrusions as operative coupling means between the tubular members provides for a mechanically simpler construction as no decoupling means are required for shifting the device between a dose setting state and a dose injection state. Furthermore, a dose setting and ejection cycle can be executed simply by rotating the first tubular member to a stop and thereafter pushing the first tubular member axially in a distal direction to a stop. The first tubular member may be provided with a dose knob at its proximal end to ease the operation.

In another embodiment of the invention an injection device for delivering a predetermined fixed dose of liquid drug is provided, the injection device comprising:
- a base member,
- a piston rod adapted to cooperate with a piston in causing the predetermined fixed dose to be delivered from the device,
- a first tubular member engaging the base member via a first track and a first protruding part, one of the first track and the first protruding part being arranged on an outer surface of the first tubular member, and the other of the first track and the first protruding part being arranged on the base member, said first protruding part engaging the first track, the first tubular member being movable to set the predetermined fixed dose,
- a second tubular member engaging the first tubular member via a second track and a second protruding part, one of the second track and the second protruding part being arranged on an outer surface of the second tubular member, and the other of the second track and the second protruding part being arranged on an inner surface of the first tubular member, said second protruding part engaging the second track, the second tubular member further being threadedly connected to the piston rod, wherein the first track comprises a first portion which the first protruding part travels during setting of the predetermined fixed dose, and the second track comprises a first portion which the second protruding part travels during setting of the predetermined fixed dose, and wherein the first portion of the first track and the first portion of the second track are shaped in such a manner that, during setting of the predetermined fixed dose, angular and axial movements of the first tubular member relatively to the base member correspond to angular and axial movements of the first tubular member relatively to the second tubular member.

In the present context the term 'predetermined fixed dose' should be interpreted in such a manner that the injection device is only capable of setting and delivering a specific fixed dose, i.e. the dose delivered by the injection device is not variable and settable by the user. Thus, the injection device is designed in such a way that attempts to deliver a dose of drug which differs from the predetermined fixed dose will fail, i.e. no drug will be delivered if another dose than the correct predetermined fixed dose has been set. Furthermore, once the predetermined fixed dose has been set and the injection has commenced, it is not possible to stop the injection before the entire set dose has been injected. Or it is at least not possible to start setting a new dose before injection of the previous dose has been fully completed.

In the present context the term 'liquid drug' should be interpreted to mean a medical drug which is in liquid form under normal storage conditions and under normal delivery conditions, i.e. substantially room temperature and atmospheric pressure. Examples of suitable liquid drugs could be human growth hormone (HGH) or a fluid pharmaceutical formulation comprising a glucagon-like peptide (GLP) compound used for treating type II diabetes, such as a GLP-1 compound or a GLP-2 compound.

As used herein, the term 'drug' is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

In the present context, the term 'zero dose position' should be interpreted as a position in which no dose is set, i.e. corresponding to either a completely new and unused device or a device which has just completed an ejection of the predetermined fixed dose. In terms of axial position of the first tubular member the 'zero dose position' corresponds to the ejection stop position.

The injection device of the present invention is suitable for self-injection because it is easy and intuitive to use. Accordingly it can be operated by a user without any specific medical skills. The injection device may be a disposable device containing a specific amount of liquid drug. In this case the injection device is disposed of once the liquid drug contained in the device has been delivered. Alternatively, the injection device may be a durable device in which a cartridge containing a desired liquid drug can be inserted. When the liquid drug of the cartridge has been delivered, the cartridge is, in this case, replaced by a new, full cartridge. In durable devices it must be possible to return the piston rod to an initial position during cartridge replacement. This ensures that the device is ready for delivering drug from the new cartridge.

The injection device comprises a piston rod adapted to cooperate with a piston in causing the predetermined fixed dose to be delivered from the device. The piston rod may advantageously be an elongated member arranged in abutment with a piston arranged in a cartridge containing the liquid drug. When a dose of drug is delivered by the injection device, the piston rod is caused to move in such a manner that it pushes the piston in a distal direction, the piston being moved a distance corresponding to the predetermined fixed dose, the dose thereby being delivered via a needle arranged at the distal end of the cartridge. This is known per se.

The base member is a member, which may be arranged in such a manner that it substantially surrounds the first tubular member and the second tubular member or at least partly covers the outer surface of the first tubular member. Alternatively, the base member may be arranged in such a manner that it is substantially surrounded by at least one of the first tubular member and the second tubular member. The base member may be or form part of a housing of the injection device. Alternatively, the base member may be a separate member arranged as described above. In this case the base member may be fixed or locked to a housing of the injection device, rotationally and/or axially. Alternatively, the base member may be completely disconnected from the housing.

In a particular embodiment of the invention, the base member is a member, which is arranged in such a manner that it substantially surrounds the first tubular member and the second tubular member.

The first tubular member has a tubular shape, preferably a cylindrical shape, i.e. it defines a hollow part. The first tubular member engages the base member via a first track and a first protruding part. In the present context the term 'engage' should be interpreted to mean that the first protruding part is received in the first track in such a manner that when first tubular member perform relative movements with respect to the base member, the first protruding part is confined to move along the first track. Thus, relative movements between the first tubular member and the base member are determined and limited by the shape and size of the first track. One of the first track and the first protruding part is arranged on an outer surface of the first tubular member, while the other one is arranged on the base member. This should be understood in the following manner. In the case that the first track is arranged on an outer surface of the first tubular member, the first protruding part is arranged on the base member. On the other hand, in the case that the first track is arranged on the base member, the first protruding part is arranged on an outer surface of the first tubular member. It is preferred that the first track is arranged on an outer surface of the first tubular member and the first protruding part is arranged on the base member, since this makes it easier to manufacture the device. However, the reverse situation could also be realised, and it should therefore be considered to be within the scope of protection of the present invention.

The first tubular member may advantageously be or form part of a driver for the injection device.

Similarly, the second tubular member engages the first tubular member via a second track and a second protruding part. One of the second track and the second protruding part is arranged on an outer surface of the second tubular member, and the other one is arranged on an inner surface of the first tubular member. The remarks set forth above regarding the positions of the first track and the first protruding part, as well as the remarks regarding engagement between the first tubular member and the base member are equally applicable to the positions of the second track and the second protruding part and to the engagement between the second tubular member and the first tubular member.

The second tubular member may advantageously be or form part of a piston rod guide (PRG) for the injection device.

The first tubular member, the second tubular member and the base member are preferably arranged mutually circumferentially, e.g. coaxially, most preferably in such a manner that the second tubular member is arranged closest to a centre part of the injection device, and in such a manner that the first tubular member is arranged between the second tubular member and the base member.

It is clear from the description above that the first tubular member engages the base member as well as the second tubular member via the tracks and the protruding parts.

Thus, moving the first tubular member causes both of the protruding parts to travel the corresponding track.

The first tubular member is movable, preferably manually, to set the predetermined fixed dose. Thus, the first tubular member may comprise or be connected to a manipulable part which a user may rotate or otherwise manipulate when it is desired to set and inject a fixed dose of liquid drug, thereby causing a desired movement of the first tubular member. This movement results in the predetermined fixed dose being set.

The second tubular member may be rotationally locked to the piston rod. In that case, the second tubular member and the piston rod are not capable of performing relative rotational movements. Thus, if the second tubular member rotates, the piston rod is forced to rotate along.

The first track comprises a first portion which the first protruding part travels during setting of the predetermined fixed dose. Similarly, the second track comprises a first portion which the second protruding part travels during setting of the predetermined fixed dose. Accordingly, when the first tubular member is moved during setting of the predetermined fixed dose, this movement causes the first protruding part to travel the first portion of the first track and the second protruding part to travel the first portion of the second track.

The first portions of the first and second track, respectively, are shaped in such a manner that, during setting of the predetermined fixed dose, angular and axial movements of the first tubular member relatively to the base member correspond to angular and axial movements of the first tubular member relatively to the second tubular member. In the present context the term 'corresponding to' should be interpreted to mean that the tracks are shaped in such a manner that, during setting of the predetermined fixed dose, the base member and the second tubular member do not perform relative movements. Thus, the relative movements between the first tubular member/base member and the second tubular member/first tubular member could be regarded as identical. In particular, the second tubular member is not rotated relatively to the base member during setting of the predetermined fixed dose, and thereby the piston rod does not perform rotational movements relatively to the base member during setting of the dose.

This is an advantage because the mere geometry of the tracks prevents movements, in particular rotational movements, of the piston rod during setting of the predetermined fixed dose. Thereby unintentional delivery of drug during setting of the dose is prevented in an easy manner, and without the requirement of complicated clutch arrangements or the like.

Furthermore, it is possible to reverse the movement of the first tubular member, thereby causing the first and second protruding part to travel the first portion of their respective track in a reversed direction. This will cause a decrease in the set amount, and it is thereby possible to cancel the dose.

The second tubular member may be adapted to rotate during injection of a previously set dose, and the sum of an angle rotated by the first tubular member relative to the base member during dose setting and the angle rotated by the second tubular member relative to the base member during injection of a previously set dose may, in this case, equal 360°. According to this embodiment it is ensured that the relative angular movement between the first tubular member and the second tubular member during a complete cycle of setting and injecting the predetermined fixed dose is 360°, i.e. a full revolution. Accordingly, the injection device is immediately ready for a new cycle. The angle rotated by the first tubular member relative to the base member during dose setting may be 180°, in which case the angle rotated by the second tubular member relative to the base member during injection of a previously set dose must also be 180°. As an alternative, the angle rotated by the first tubular member may be 120°, in which case the angle rotated by the second tubular member must be 240°. As another alternative, the angle rotated by the first tubular member may be 240°, in which case the angle rotated by the second tubular member must be 120°.

In alternative embodiments, the sum of an angle rotated by the first tubular member relative to the base member during dose setting and the angle rotated by the second tubular member relative to the base member during injection of a previously set dose may be different from 360°. In any case, the first and second tracks must be arranged such that upon completion of a dose setting and injection cycle, the injection device is immediately ready for a new cycle.

The first portion of the first track may define a helical path on the outer surface of the first tubular member or on an inner surface of the base member, and the first portion of the second track may define a helical path on the outer surfaces of the second tubular member or on the inner surface of the first tubular member. Alternatively, the first portions of the respective tracks may have any other suitable shape, such as piecewise linearly, e.g. having a portion which is arranged along an axial direction of the injection device and a portion which is arranged substantially annularly on a suitable tubular member, or the tracks may define curved paths of a more irregular shape. In any event it should be ensured that the first portion of the first track and the first portion of the second track are shaped in such a manner that the second tubular member and the base member do not perform relative movements during setting of the predetermined fixed dose, as described above.

The first track may comprise a second portion which the first protruding part travels during injection of a previously set dose, and the second track may comprise a second portion which the second protruding part travels during injection of a previously set dose. The second portion of the first track preferably differs from the second portion of the second track, thereby allowing relative movements between the base member and the second tubular member during injection of a dose. Thereby the piston rod is also allowed to rotate relatively to the base member during injection of a dose.

The second portion of the first track may, in this case, define a substantially linear path on the outer surface of the first tubular member or on an inner surface of the base member, and along an axis defined by the first tubular member. According to this embodiment, the first tubular member is not rotated relative to the base member during injection of a previously set dose. Accordingly, the relative movement between the first tubular member and the base member during injection is purely axial. This is an advantage in the case that the first tubular member is pressed in a distal direction in order to cause a set dose to be injected, because the user will thereby not feel a rotation of the first tubular member during the injection.

The second portion of the second track may define a substantially helical path on the outer surface of the second tubular member or on the inner surface of the first tubular member. According to this embodiment, the second tubular member performs movements having a rotational component during injection of a previously set dose. Accordingly, the piston rod is rotated during injection of a dose.

The first track and the second track may each comprise a coupling portion interconnecting the first portion and the second portion. According to this embodiment, the first/second protruding part must be moved along the coupling portion of the corresponding track in order to shift the injection device from a state in which it is possible to set a dose and a state in which it is possible to inject a previously set dose. Since the coupling portions form part of the tracks, it is not possible to perform this shift before the predetermined fixed dose has been set, i.e. it is not possible to inject an incorrect dose, e.g. an insufficient dose. In particular, if it is intended to inject drug before the protruding parts have reached the end of the respective first portions of the tracks, and thereby the respective coupling portions, the protruding parts will simply return along the first portions of the respective tracks. Thereby the second tubular member is not moved relatively to the base member during such an operation, and no drug is delivered. Thus, in a simple manner it is prevented that an insufficient dose of drug is delivered.

The injection device may further comprise a nut member being axially and rotationally locked relative to the base member and being threadedly connected to the piston rod in such a manner that when the second tubular member is rotationally locked to the piston rod, a rotation of the second tubular member causes a rotation of the piston rod which then causes the piston rod to move in an axial direction relative to the base member. According to this embodiment, rotational movements of the piston rod relatively to the base member results in the piston rod performing a spiraling movement, preferably in a distal direction, due to the threaded connection. The axial movement of the piston rod may advantageously be used for pushing the piston in a distal direction, thereby causing liquid drug to be delivered as described above. The axial distance traveled by the piston rod during rotation of a specific angle is determined by the pitch of the thread. Accordingly, the amount of liquid drug constituted by a predetermined fixed dose can be selected by designing the pitch of the thread in an appropriate manner. Alternatively or additionally, the concentration of the drug contained in the cartridge may be used for determining the predetermined fixed dose being delivered by the injection device.

Alternatively, the injection device may further comprise a guide member being axially and rotationally locked with respect to the base member and being rotationally locked with respect to the piston rod in such a manner that when the second tubular member is threadedly connected to the piston rod, rotation of the second tubular member causes the piston rod to move non-rotationally in an axial direction relative to the base member. The axial movement of the piston rod may advantageously be used for pushing the piston in a distal direction, thereby causing liquid drug to be delivered as described above. Again, the axial distance traveled by the piston rod during rotation of a specific angle is determined by the pitch of the thread.

The injection device may further comprise means for providing an audible and/or tactile feedback signal when injection of a previously set dose has been completed. According to this embodiment, the user will readily know when the injection has been completed and the needle can be removed, even if the user is visually impaired, or the injection site is at a position which is not readily visible to the user during injection.

In this case the means for providing an audible and/or tactile feedback signal may comprise an abrupt change of pitch of the second track. In this case the user feels an acceleration in an axial direction during the last part of the injection, and an abrupt stop when the second protruding part reaches the end of the second portion of the second track. This abrupt stop may further give rise to an audible 'click', thereby even further informing the user that the injection has been completed.

As mentioned above, the base member may advantageously form a housing of the injection device, or form part of a housing of the injection device. Alternatively, the base member may be a separate member as described above.

In a further aspect of the invention, a method for delivering a predetermined fixed dose of liquid drug from an injection device is provided, the method comprising:

providing a device comprising:
  a base member,
  a variable volume reservoir adapted to contain the liquid drug and comprising an outlet,
  a piston rod defining a longitudinal axis and being adapted to cooperate with a piston in causing the predetermined fixed dose to be delivered from the variable volume reservoir,
  a first tubular member operatively coupled with the base member and movable to set the predetermined fixed dose,
  a second tubular member operatively coupled with the first tubular member and the piston rod, and
  means for preventing setting of a new dose once the predetermined fixed dose has been set and the ejection has commenced until the entire predetermined fixed dose has been ejected,
rotating the first tubular member from a zero dose position to a predefined dose setting stop to set the predetermined fixed dose, and
non-rotationally advancing the first tubular member along the longitudinal axis to eject the predetermined fixed dose through the outlet.

BRIEF DESCRIPTION OF THE DRAWINGS

The invention will now be described in further detail with reference to the accompanying drawings in which FIGS. 9a and 9b show various views of the injection device of FIGS. 1-8 during injection of a dose.

DETAILED DESCRIPTION OF THE DRAWINGS

Figure 1:
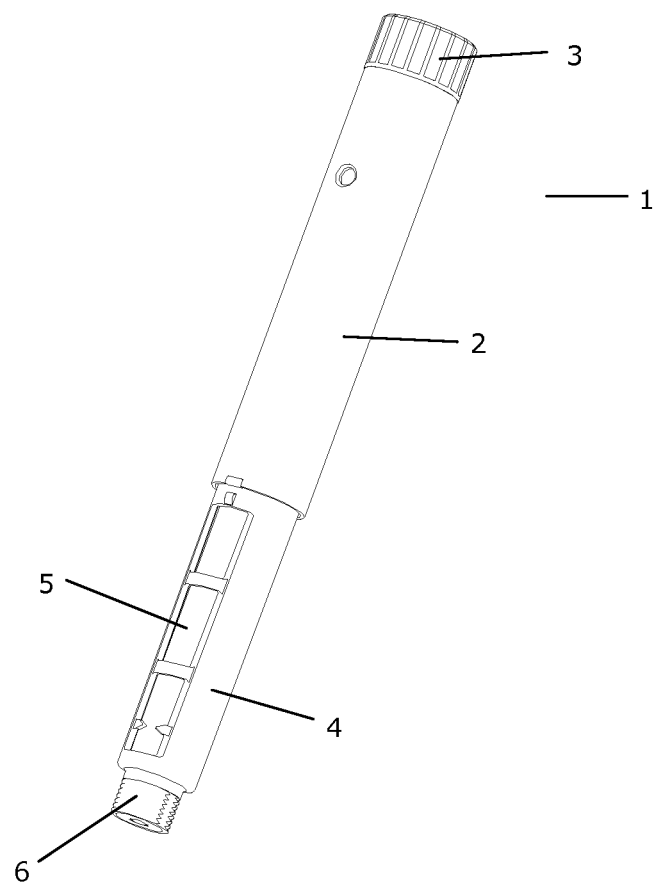
FIG. 1 is a perspective view of an injection device according to an embodiment of the invention.

FIG. 1 is a perspective view of an injection device 1 according to an embodiment of the invention. The injection device comprises a housing 2, a type of base member, a dose knob 3 being manipulable to set a fixed dose, a cartridge holder 4 holding a cartridge 5 containing a drug to be delivered and a threaded portion 6 for attaching an injection needle.

Figure 2:
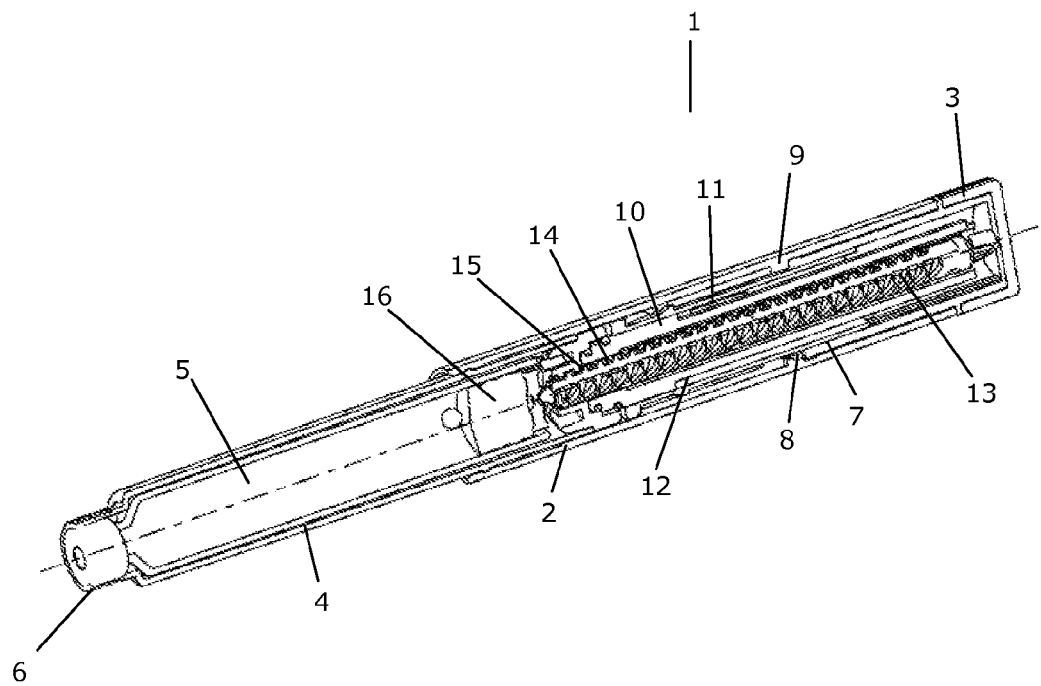
FIG. 2 is a cross sectional view of the injection device of FIG. 1, the injection device being ready to set a dose.

FIG. 2 is a cross sectional view of the injection device 1 of FIG. 1. It can be seen that the dose knob 3 is integral with a first tubular member 7 arranged inside the housing 2. The first tubular member 7 is provided with a first track 8 arranged on an outer surface of the first tubular member 7. A first protruding part 9 is arranged on an inner surface of the housing 2 in such a manner that it engages the first track 8.

The injection device 1 further comprises a second tubular member 10 arranged inside the first tubular member 7. The second tubular member 10 is provided with a second track 11 arranged on an outer surface of the second tubular member 10. A second protruding part 12 is arranged on an inner surface of the first tubular member 7 in such a manner that it engages the second track 11.

The second tubular member 10 is rotationally locked to a piston rod 13 due to a non-circular cross section of the piston rod 13 and a corresponding non-circular cross section of an opening 14 of the second tubular member 10, said opening 14 receiving the piston rod 13.

The piston rod 13 advances through the housing 2 via a threaded connection 15. Thus, when the piston rod 13 is rotated it will also move axially, thereby cooperating with a piston 16 arranged in the cartridge 5, thereby causing a dose of drug to be delivered from the injection device 1.

It is clear that the advancement of the piston rod 13 through the housing 2 could just as well be realised by providing a threaded connection between the second tubular member 10 and the piston rod 13 while rotationally locking the piston rod 13 with respect to the housing 2. In that case a rotation of the second tubular member 10 would result in the piston rod 13 being non-rotationally pushed forward in the housing 2.

In FIG. 1 the injection device 1 is shown in a state where it is ready for setting a dose. When it is desired to set a dose, the dose knob 3 is rotated, thereby causing rotation of the first tubular member 7. As a consequence, the first protruding part 9 travels along the first track 8 and the second protruding part 12 travels along the second track 11. Due to the special paths defined by the first track 8 and the second track 11, respectively, which will be described further below, the second tubular member 10 does not rotate during this operation. As a consequence, the piston rod 13 is prevented from rotating, and it is thereby avoided that drug is accidentally spilled during dose setting.

The dose knob 3 is rotated in this manner until a predetermined fixed dose has been set. At this point the protruding parts 9, 12 enter parts of the tracks 8, 11 which the protruding parts 9, 12 travel during injection of a previously set dose. If the dose knob 3 is rotated a smaller distance, corresponding to a smaller dose, the protruding parts 9, 12 will simply return via the tracks 8, 11, and the piston rod 13 is prevented from rotating as described above. Consequently, no drug is delivered, i.e. it is not possible to inject a dose which is smaller than the predetermined fixed dose. On the other hand, it is not possible to set a dose which is larger than the predetermined fixed dose, because it is not possible to rotate the dose knob 3 further than the distance corresponding to the predetermined fixed dose. Thus, the injection device 1 is only capable of delivering the predetermined fixed dose of drug.

Figure 3:
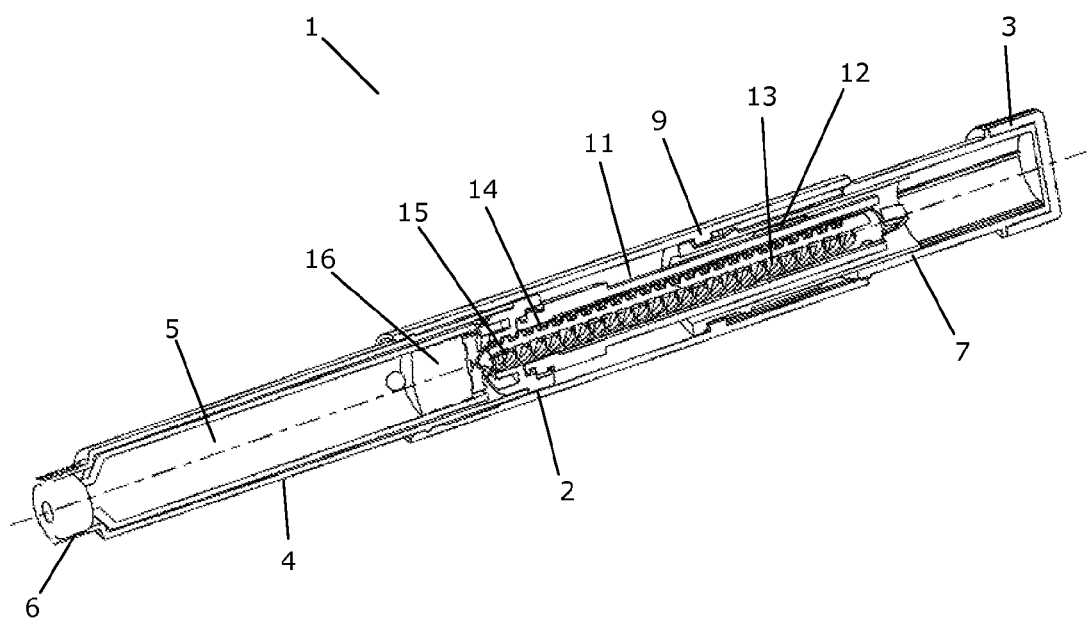
FIG. 3 is a cross sectional view of the injection device of FIGS. 1 and 2, in a state where a dose has been set and is ready to be injected.

FIG. 3 is a cross sectional view of the injection device 1 of FIGS. 1 and 2 in a state where the fixed dose has been set, and the injection device 1 is ready for injecting the previously set dose. It can be seen that the dose knob 3 and the first tubular member 7 have been moved axially in a proximal direction, i.e. out of the housing 2. When it is desired to inject the previously set dose the dose knob 3 is pushed in a distal direction, i.e. towards the housing 2. Due to the special paths defined by the portion of the tracks 8, 11 which is followed by the protruding parts 9, 12 during injection, the first tubular member 7 performs a purely axial movement, while the second tubular member 10 performs a purely rotational movement. Accordingly, the piston rod 13 rotates, and is therefore moved axially via the threaded connection 15, thereby causing the previously set dose to be delivered by the injection device 1.

Figure 4:
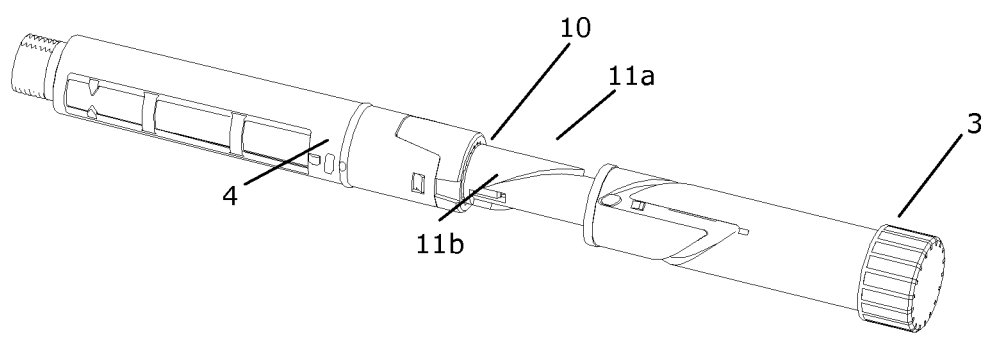

FIG. 4 is a perspective view of the injection device 1 of FIGS. 1-3. For the sake of clarity and in order to properly illustrate the second tubular member 10, the housing, the dose knob and part of the first tubular member have been removed. The position of the second track 11 on the outer surface of the second tubular member 10 can be seen. The second track 11 comprises a first portion 11a which is traveled by the second protruding part during setting of a dose, and a second portion 11b which is traveled by the second protruding part during injection of a previously set dose. The first portion 11a as well as the second portion 11b defines a substantially helical path. However, at the distal end of the second portion 11b the pitch of the track 11 changes abruptly. This has the consequence that axial velocity of the second protruding part, and thereby of the first tubular member and the dose knob which the user is pushing, increases abruptly. The user can register this abrupt increase in velocity, as well as the abrupt stop when the end of the track 11b is reached, and a tactile signal indicating that the injection has been completed is thereby provided. Furthermore, when the second protruding part hits the end of the track 11b a 'click' may be generated, thereby providing an audible signal in addition to the tactile signal.

Figure 5:
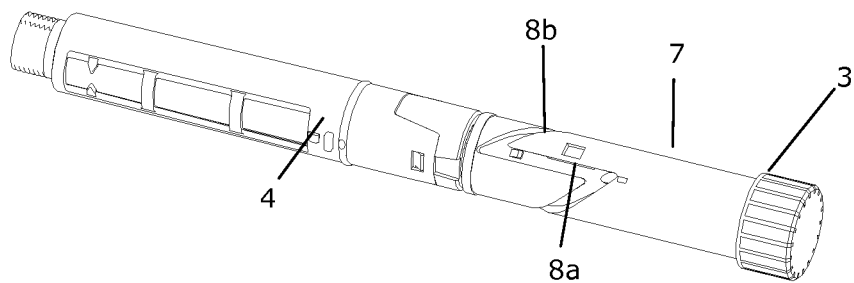
FIGS. 4 and 5 are partial views of the injection device of FIGS. 1-3, illustrating various components of the injection device.

FIG. 5 is a perspective view of the injection device 1 of FIGS. 1-4. For the sake of clarity and in order to properly illustrate the first tubular member 7, the housing has been removed. The position of the first track 8 on the outer surface of the first tubular member 7 can be seen. The first track 8 comprises a first portion 8a which is traveled by the first protruding part during setting of a dose, and a second portion 8b which is traveled by the first protruding part during injection of a previously set dose. The first portion 8a defines a substantially helical path having a pitch which is identical to the pitch of the first portion 11a of the second track 11 shown in FIG. 4. The second portion 8b defines a substantially linear path, extending along an axial direction.

Thus, during setting of a dose, the dose knob 3 is rotated, thereby causing the first protruding part to travel along the first portion 8a of the first track 8 and the second protruding part to travel along the first portion 11a of the second track 11. Since the first portion 8a of the first track 8 and the first portion 11a of the second track 11 define helical paths having identical pitch, this will not cause movement of the second tubular member 10. During injection of a previously set dose the first tubular member 7 is pushed axially, the first protruding part travelling along the second portion 8b of the first track 8. This causes the second protruding part to travel along the second portion 11b of the second track 11. Since the second portion 11b of the second track 11 is substantially helical, this will cause rotation of the second tubular member 10, and thereby of the piston rod 13, thereby moving the piston rod 13 axially through the threaded connection (not shown) and causing injection of the previously set dose.

Figures 6A, 7A, 8A:
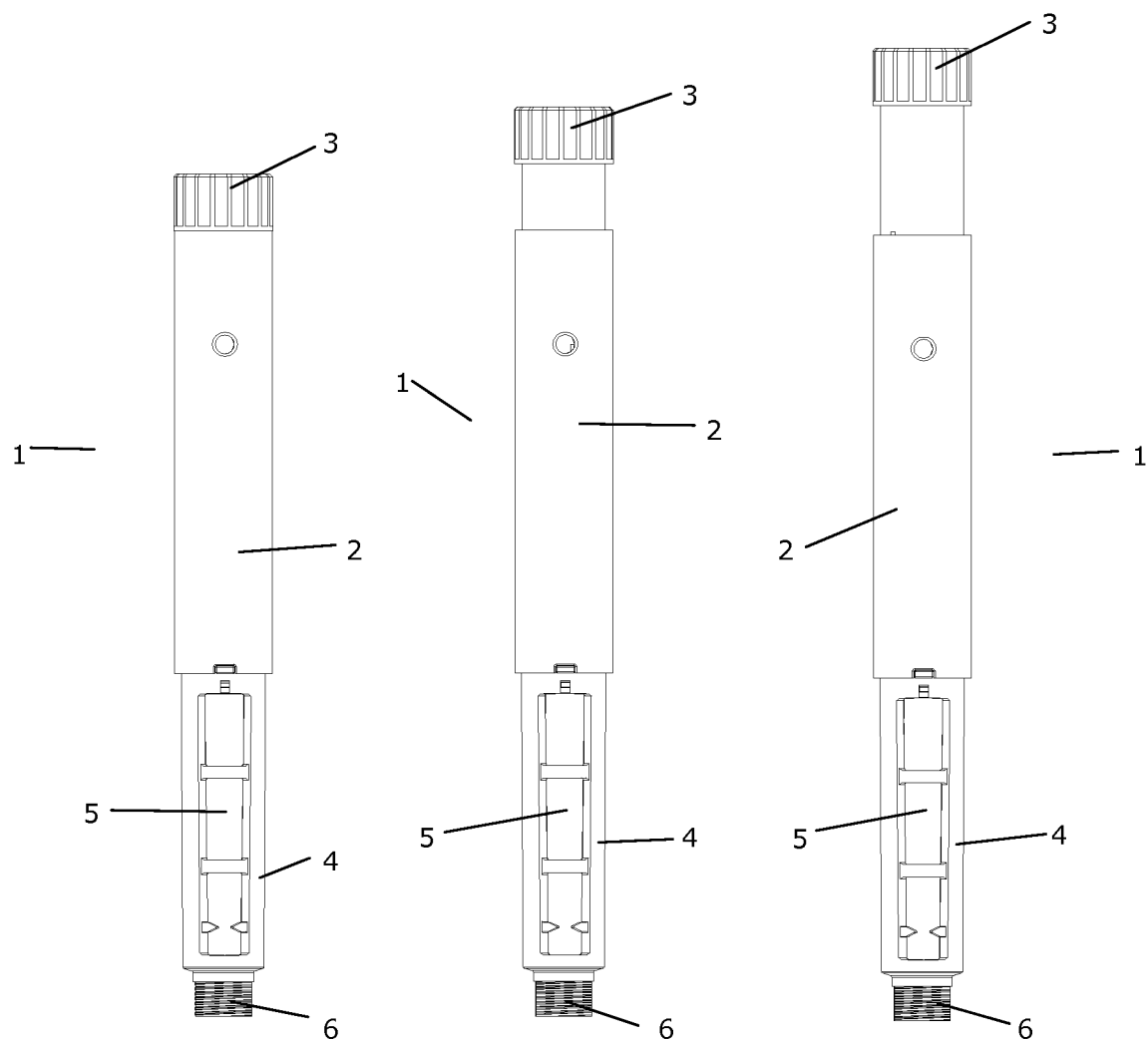
FIGS. 6a-6c show various views of the injection device of FIGS. 1-5, the injection device being ready to set a dose.
FIGS. 7a-7c show various views of the injection device of FIGS. 1-6 during setting of a dose.
FIGS. 8a-8c show various views of the injection device of FIGS. 1-7, in a state where a dose has been set and is ready to be injected.

FIG. 6a is a side view of the injection device 1 of FIGS. 1-5. It is clear that the dose knob 3 is arranged as close to the housing 2 as possible, thereby indicating that the injection device 1 is ready to set a dose. This has already been described with reference to FIGS. 1 and 2.

Figures 6B, 6C:
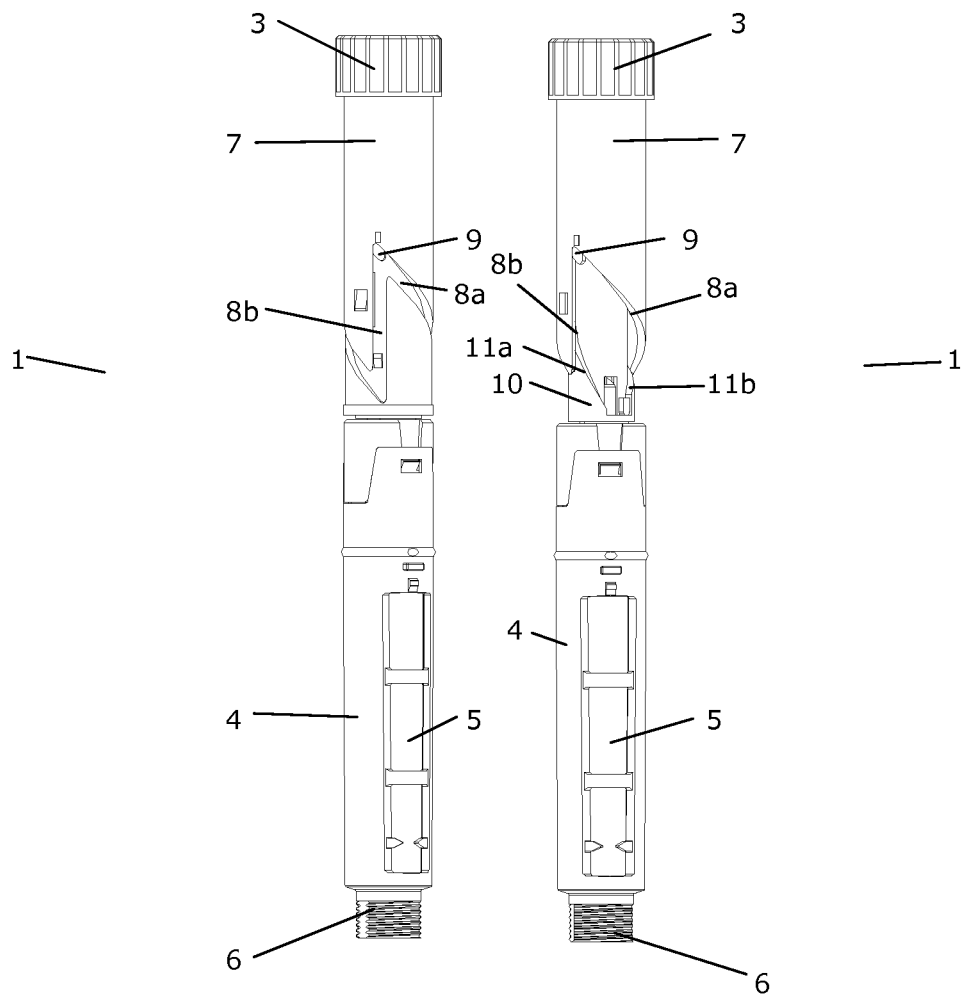

FIG. 6b shows the injection device 1 of FIG. 6a. In FIG. 6b the housing has been removed in order to show the position of the first tubular member 7 and the first track 8. Please note that the first protruding part 9, which is visible in FIG. 6b, is in fact a part of the housing. It is clear from FIG. 6b that the first protruding part 9 is positioned adjacent to the first portion 8a of the first track 8. Thus, rotating the dose knob 3, and thereby the first tubular member 7, in a direction towards the left in FIG. 6b will cause the first protruding part 9 to follow the first portion 8a of the first track 8. Due to the helical shape of the first portion 8a of the first track 8, the first tubular member 7 and the dose knob 3 move in a proximal direction, i.e. upwards in FIG. 6b. This causes a dose to be set.

FIG. 6c shows the injection device 1 of FIGS. 6a and 6b. In FIG. 6c part of the first tubular member 7 has further been removed in order to show the position of the second tubular member 10 and the second track 11. The second protruding part is not visible in FIG. 6c, but it is arranged on an inner surface of the first tubular member 7, and it is positioned adjacent to the first portion 11a of the second track 11. Accordingly, when the dose knob 3, and thereby the first tubular member 7, are rotated as described above the second protruding part travels the first portion 11a of the second track 11. It can be seen from FIG. 6c that the pitch of the first portion 8a of the first track 8 is identical to the pitch of the first portion 11a of the second track 11. Thus, when the first tubular member 7 is rotated the path traveled by the first protruding part 9 is identical to the path traveled by the second protruding part 12, and thereby the second tubular member 10 remains immobile relative to the first protruding part 9, and thereby to the housing 2 having the first protruding part 9 arranged thereon.

FIG. 7a is a side view of the injection device 1 of FIGS. 1-6. In FIG. 7a the dose knob 3 has been moved slightly in a proximal direction, i.e. upwards in the Figure, thereby indicating that a dose is in the progress of being set.

Figures 7B, 7C:
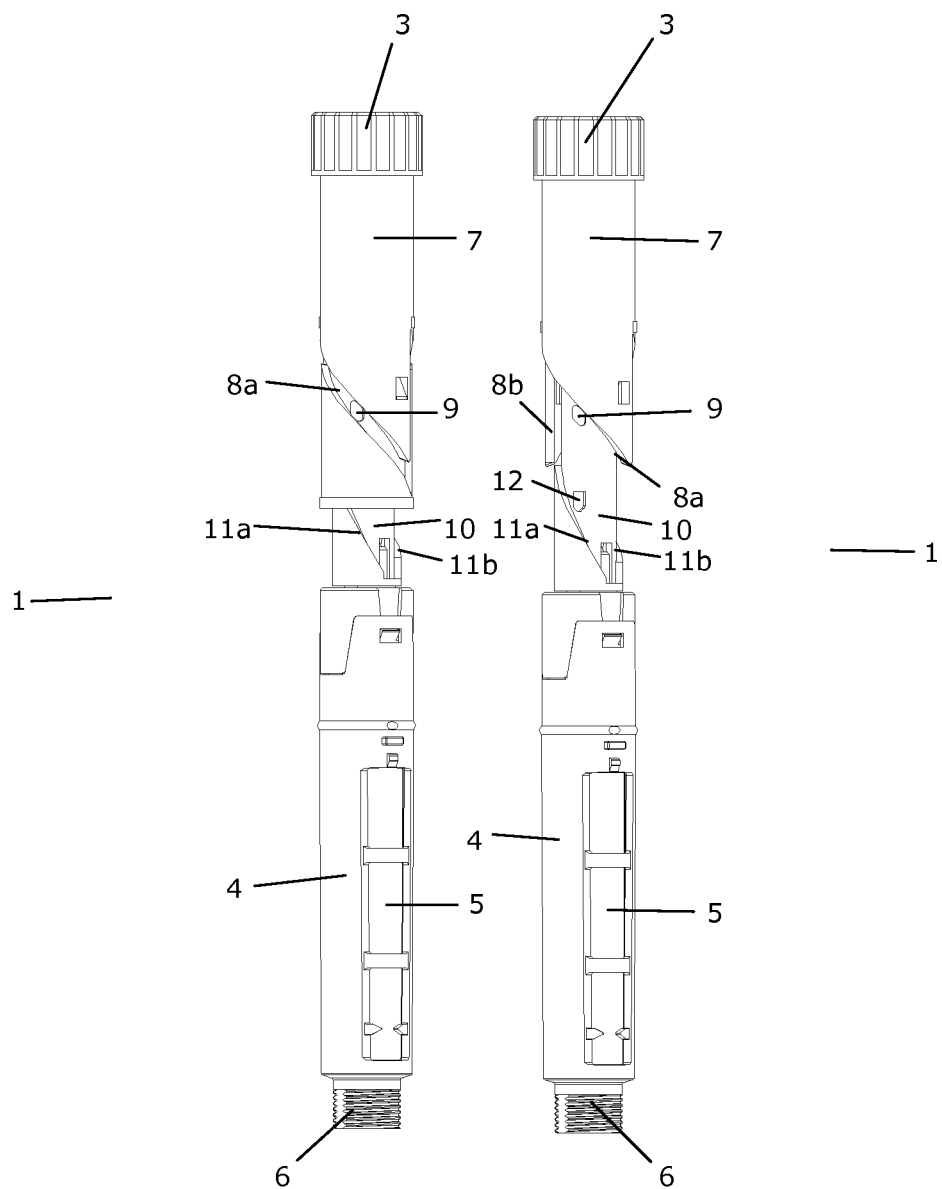

FIG. 7b shows the injection device 1 of FIG. 7a. In FIG. 7b the housing has been removed in order to show the position of the first tubular member 7 and the first track 8. It is clear that the first protruding part 9 is arranged at a position along the first portion 8a of the first track 8. Comparing FIG. 6b and FIG. 7b it is clear that this position has been reached by rotating the first tubular member as described above. Rotating the first tubular member 7 further in the same direction will cause the first protruding part 9 to travel even further along the first portion 8a of the first track 8 until the end of the first portion 8a is reached. When the end position is reached the predetermined fixed dose has been set. On the other hand, as long as the first protruding part 9 is positioned along the first portion 8a of the first track 8, a reverse rotation of the first tubular member 7 is possible, thereby cancelling the set dose. Furthermore, pressing the dose knob 3 in a distal direction, i.e. downwards in the Figure, will also cause the first protruding part 9 to return along the first portion 8a of the first track 8, i.e. the set dose is cancelled and no drug is injected.

FIG. 7c shows the injection device 1 of FIGS. 7a and 7b. In FIG. 7c part of the first tubular member 7 has been removed in order to show the position of the second tubular member 10 and the second track 11. Please note that the second protruding part 12, which is visible in FIG. 7c, is in fact a part of the first tubular member. It can be seen that the second protruding part 12 is arranged at a position along the first portion 11a of the second track 11.

FIG. 8a is a side view of the injection device 1 of FIGS. 1-7. In FIG. 8a the dose knob 3 has been moved even further in a proximal direction, i.e. upwards in the Figure, thereby indicating that dose setting has been completed.

Figures 8B, 8C:
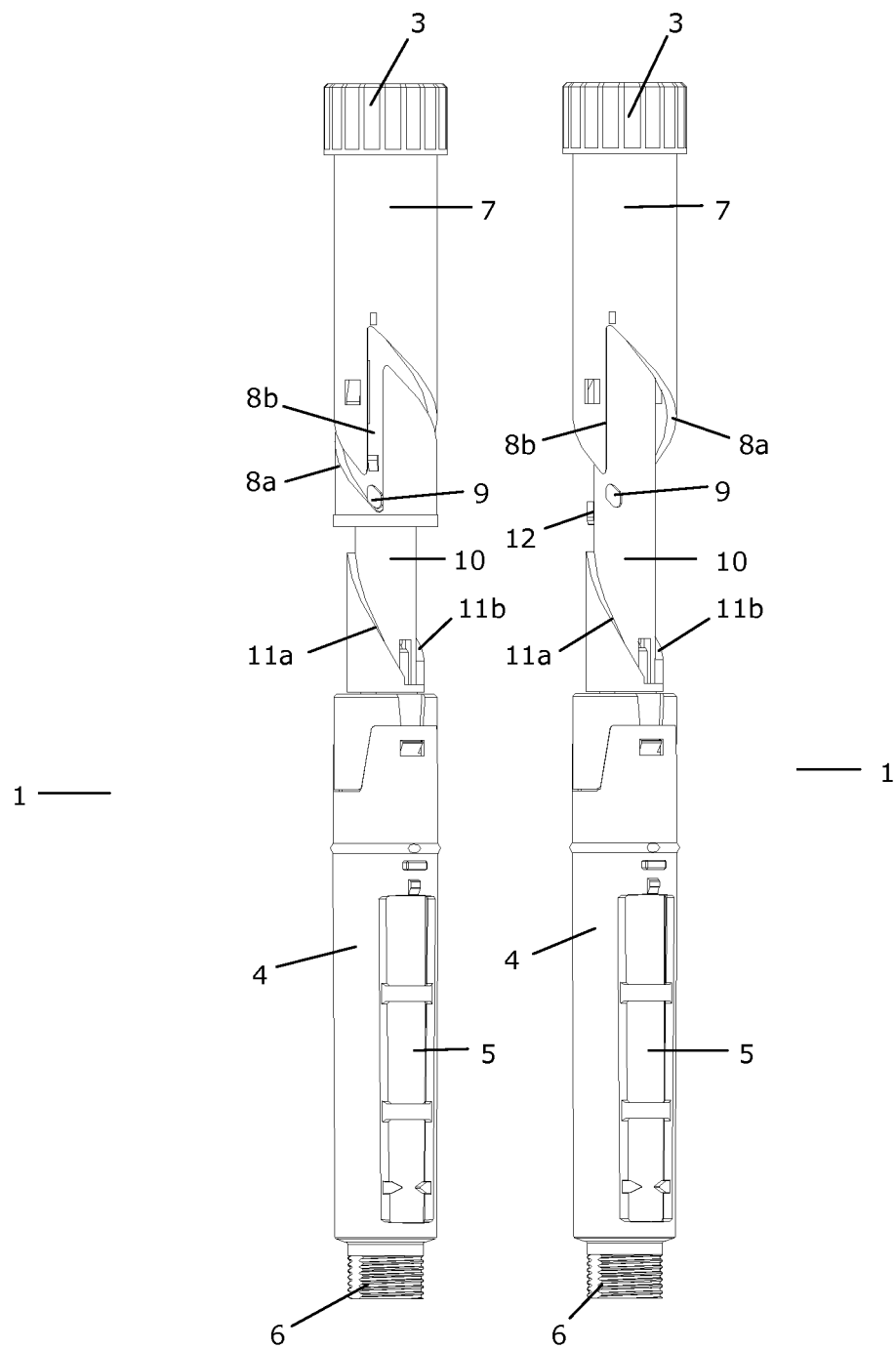

FIG. 8b shows the injection device 1 of FIG. 8a. In FIG. 8b the housing has been removed in order to show the position of the first tubular member 7 and the first track 8. It is clear that the first protruding part 9 is arranged at a position at the end of the first portion 8a of the first track 8 and adjacent to the second portion 8b of the first track 8. Thus, it is not possible to rotate the first tubular member 7 further in the direction defined above. Pushing the dose knob 3 in a distal direction, i.e. downwards in the Figure, causes the first protruding part 9 to travel along the second portion 8b of the first track 8. Since the second portion 8b of the first track 8 is substantially linear in an axial direction, the first tubular member 7 is thereby moved axially during this movement. The axial movement of the first tubular member 7 causes the set dose to be injected. This will be explained further below.

FIG. 8c shows the injection device 1 of FIGS. 8a and 8b. In FIG. 8c part of the first tubular member 7 has further been removed in order to show the position of the second tubular member 10 and the second track 11. It can be seen that the second protruding part 12 is arranged at the end of the first portion 11a of the second track 11 and adjacent to the second portion 11b of the second track 11. The second portion 11b of the second track 11 has a helical shape. This is seen more clearly in FIG. 9b. When the first tubular member 7 is moved axially as described above, the second protruding part 12 travels along the second portion 11b of the second track 11. Due to the helical shape of the second portion 11b of the second track 11, the second tubular member 10 is forced to rotate during this movement. The second tubular member 10 is rotationally locked to a piston rod (not visible) which is further threadedly engaged in a nut (not visible) which is at least rotationally locked to the housing. Accordingly, the rotating movement of the second tubular member 10 causes the piston rod to rotate, and the threaded connection causes the piston rod to move in a distal direction. Thereby the piston rod pushes a piston (not visible) arranged in the cartridge 5 in a distal direction, and a dose of drug is delivered via a needle (not shown) attached to the threaded portion 6.

FIG. 9a shows the injection device 1 of FIGS. 1-8. In FIG. 9a the housing has been removed in order to show the position of the first tubular member 7 and the first track 8. In FIG. 9a the dose knob 3 and the first tubular member 7 have been moved slightly in a distal direction, as compared to the situation shown in FIG. 8. It can be seen that the first protruding part 9 is arranged at a position along the second portion 8b of the first track 8. Accordingly, the first tubular member 7 has been moved to this position by an axial movement, and a previously set dose is in the process of being injected as described above.

FIG. 9b shows the injection device of FIG. 9a. In FIG. 9b part of the first tubular member 7 has further been removed in order to show the position of the second tubular member 10 and the second track 11. It can be seen that the second protruding part 12 is arranged at a position along the second portion 11b of the second track 11. It is also clear that the second portion 11b of the second track 11 has a helical shape as explained above.

Figure 10A:
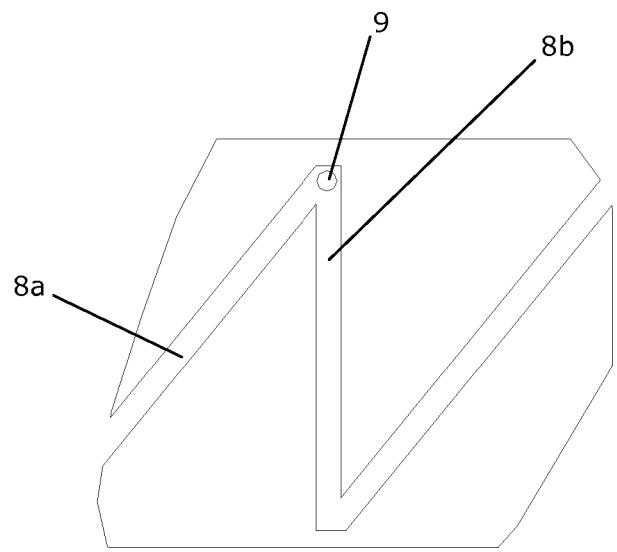
FIGS. 10a and 10b show diagrams illustrating relative movements of the first tubular member and the second tubular member during dose setting.
Figure 10B:
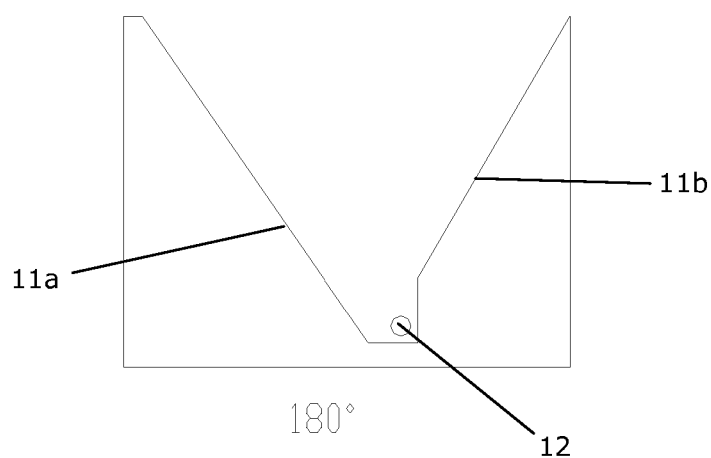
Figure 11A:
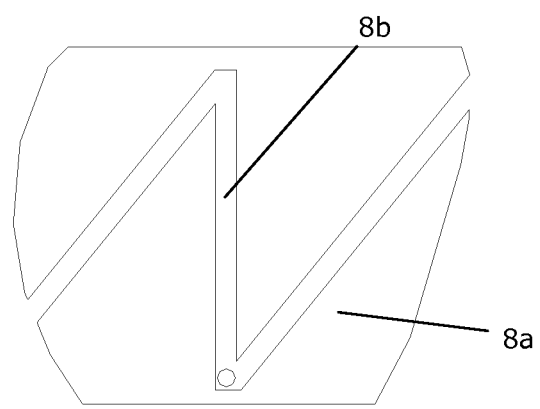
FIGS. 11a and 11b show diagrams illustrating relative movements of the first tubular member and the second tubular member during injection of a previously set dose.
Figure 11B:
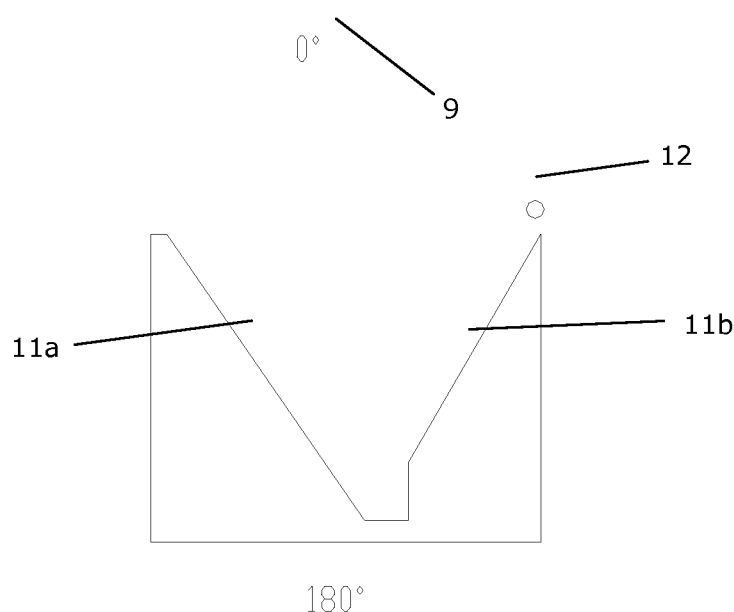

FIGS. 10a and 11a are diagrams schematically illustrating the shape of the first track 8, and FIGS. 10b and 11b are diagrams schematically illustrating the shape of the second track 11. In FIG. 10 the injection device is in a state where it is ready to set a dose. Rotating the first tubular member causes the first protruding part 9 to travel the first portion 8a of the first track 8, and the second protruding part 12 to travel the first portion 11a of the second track 11.

In FIG. 11 the injection device is in a state in which a dose has been set and is ready to be injected. Pushing the first tubular member in a distal direction causes the first protruding part 9 to travel the second portion 8b of the first track 8, and the second protruding part 12 to travel the second portion 11b of the second track 11. Since the second portion 8b of the first track 8 is substantially linear in an axial direction and the second portion 11b of the second track 11 has a helical shape, the first tubular member is moved axially relative to the housing, while the second tubular member performs a rotating movement relative to the housing.

At the end of the second portion 11b of the second track 11 the pitch is changed dramatically. When the second protruding part 12 reaches this part of the second track 11, the user will experience an acceleration in the axial movement of the dose knob, followed by an abrupt stop. Thereby the user can easily feel when the dose has been delivered, i.e. when the injection has been completed.

The invention claimed is:

1. An injection device for delivering a predetermined fixed dose of liquid drug, the injection device comprising:
    a base member,
    a piston rod defining a longitudinal axis and being adapted to cooperate with a piston in causing the predetermined fixed dose to be delivered from the device,
    a first tubular member operatively coupled with the base member and movable to set the predetermined fixed dose,
    a second tubular member operatively coupled with the first tubular member and the piston rod,
    wherein during each setting of the predetermined fixed dose the first tubular member is rotated with respect to the base member from a zero dose position to a predefined dose setting stop and during injection the first tubular member is allowed to advance non-rotationally along the longitudinal axis while the second tubular member is allowed to rotate with respect to the base member; and
    wherein the predetermined fixed dose is not variable and settable by the user.

2. An injection device according to claim 1, wherein
    the first tubular member engages the base member via a first track and a first protruding part, one of the first track and the first protruding part being arranged on an outer surface of the first tubular member, and the other of the first track and the first protruding part being arranged on the base member, said first protruding part engaging the first track, and
    the second tubular member engages the first tubular member via a second track and a second protruding part, one of the second track and the second protruding part being arranged on an outer surface of the second tubular member, and the other of the second track and the second protruding part being arranged on an inner surface of the first tubular member, said second protruding part engaging the second track.

3. An injection device according to claim 2, wherein the first track comprises a first portion which the first protruding part travels during setting of the predetermined fixed dose, and the second track comprises a first portion which the second protruding part travels during setting of the predetermined fixed dose, and wherein the first portion of the first track and the first portion of the second track are shaped in such a manner that, during setting of the predetermined fixed dose, angular and axial movements of the first tubular member relatively to the base member correspond to angular and axial movements of the first tubular member relatively to the second tubular member.

4. An injection device according to claim 1, wherein once the predetermined fixed dose has been set and the injection has commenced, it is not possible to start setting a new dose until the injection has been fully completed.

5. An injection device according to claim 1, wherein the sum of an angle rotated by the first tubular member relative to the base member during dose setting and the angle rotated by the second tubular member relative to the base member during injection of a previously set dose equals 360°.

6. An injection device according to claim 2, wherein the first portion of the first track defines a helical path on the outer surface of the first tubular member or on an inner surface of the base member, and the first portion of the second track defines a helical path on the outer surfaces of the second tubular member or on the inner surface of the first tubular member.

7. An injection device according to claim 1, further comprising a nut member being axially and rotationally locked relative to the base member and being threadedly connected to the piston rod in such a manner that when the second tubular member is rotationally locked to the piston rod, rotation of the second tubular member causes the piston rod to move in an axial direction relative to the base member.

8. An injection device according to claim 2, further comprising structure for providing an audible and/or tactile feedback signal when injection of a previously set dose has been completed.

9. An injection device according to claim 8, wherein the structure for providing an audible and/or tactile feedback signal comprises an abrupt change of pitch of the second track.

10. An injection device according to claim 1, wherein the base member forms a housing of the injection device.

* * * * *